US012551383B2

(12) United States Patent
Serrano et al.

(10) Patent No.: US 12,551,383 B2
(45) Date of Patent: Feb. 17, 2026

(54) SANITARY NAPKIN FOR HEAVY UTERINE BLEEDING

(71) Applicant: GRUPO P.I. MABE S.A. DE C.V., Puebla (MX)

(72) Inventors: Liliana Sanchez Serrano, Puebla (MX); Denisse Torres Gonzalez, Puebla (MX); Karla Paulina Hernandez Ramos, Coronango (MX)

(73) Assignee: GRUPO P.I. MABE, S.A. DE C.V., Puebla (MX)

( * ) Notice: Subject to any disclaimer, the term of this patent is extended or adjusted under 35 U.S.C. 154(b) by 1453 days.

(21) Appl. No.: 16/753,867

(22) PCT Filed: Oct. 8, 2018

(86) PCT No.: PCT/IB2018/057778

§ 371 (c)(1),
(2) Date: Apr. 6, 2020

(87) PCT Pub. No.: WO2019/073355

PCT Pub. Date: Apr. 18, 2019

(65) Prior Publication Data

US 2020/0281781 A1 Sep. 10, 2020

(30) Foreign Application Priority Data

Oct. 9, 2017 (EP) .................................... 17195397

(51) Int. Cl.
*A61F 13/511* (2006.01)
*A61F 13/47* (2006.01)
*A61F 13/56* (2006.01)

(52) U.S. Cl.
CPC ........ *A61F 13/51108* (2013.01); *A61F 13/47* (2013.01); *A61F 13/5616* (2013.01)

(58) Field of Classification Search
CPC .......................... A61F 13/51108; A61F 13/47; A61F 13/5616; A61F 13/4704; A61F 13/15203;
(Continued)

(56) References Cited

U.S. PATENT DOCUMENTS 5,201,727 A * 4/1993 Nakanishi ........... A61F 13/5616 604/389
5,795,345 A 8/1998 Mizutani et al.
7,279,613 B2 * 10/2007 Nozaki ................ A61F 13/536 604/385.16

(Continued)

FOREIGN PATENT DOCUMENTS

DE 102010015559 A1 10/2011
EP 0731681 B1 8/2000

(Continued)

OTHER PUBLICATIONS

International Search Report and Written Opinion for PCT/IB2018/057778, mailed Dec. 3, 2018.

*Primary Examiner* — Philip R Wiest
*Assistant Examiner* — Brandon W. Levy
(74) *Attorney, Agent, or Firm* — Ladas & Parry LLP

(57) ABSTRACT

A secure and discreet sanitary napkin (1) having fold back wings (3) positioned along the longitudinal sides (9) of the sanitary napkin (1) so that an overall length ratio corresponds to the equation L*(L1/L2)>29 cm, where L is the total length of the sanitary napkin (1) taken along its longitudinal central axis (y-y), L1 is the distance from the transverse axis (x-x) of the fold back wings (3) to the front edge (6) of the sanitary napkin (1), and L2 is the distance from the transverse axis (x-x) of the sanitary napkin (1) to the rear edge (7) of the sanitary napkin (1).

17 Claims, 5 Drawing Sheets

(58) Field of Classification Search
CPC ................ A61F 13/476; A61F 13/4756; A61F 2013/15365
See application file for complete search history.

(56) References Cited

U.S. PATENT DOCUMENTS

| | | | | |
|---|---|---|---|---|
| 7,686,790 | B2 | 3/2010 | Rasmussen et al. | |
| 7,708,725 | B2 | 5/2010 | Tamagawa et al. | |
| 8,715,258 | B2 | 5/2014 | Munakata et al. | |
| 8,927,803 | B2 * | 1/2015 | Sakai | A61F 13/4756 604/385.101 |
| 9,125,772 | B2 | 9/2015 | Eilers et al. | |
| 2004/0243087 | A1 * | 12/2004 | Kinoshita | A61F 13/476 604/385.04 |
| 2006/0116653 | A1 * | 6/2006 | Munakata | A61F 13/4702 604/385.101 |
| 2006/0276767 | A1 * | 12/2006 | Ueminami | A61F 13/533 604/385.101 |
| 2007/0282287 | A1 * | 12/2007 | Noda | A61F 13/5611 604/385.01 |
| 2015/0265474 | A1 | 9/2015 | Munakata et al. | |
| 2016/0250084 | A1 | 9/2016 | Umemoto et al. | |
| 2020/0121517 | A1 * | 4/2020 | Kuramochi | A61F 13/4702 |

FOREIGN PATENT DOCUMENTS

| | | | | |
|---|---|---|---|---|
| EP | 1269953 B1 | | 9/2006 | |
| EP | 2578194 A1 | | 4/2013 | |
| JP | 2009232950 A | * | 10/2009 | A61F 13/474 |
| WO | 2015068718 A1 | | 5/2015 | |

* cited by examiner

SANITARY NAPKIN FOR HEAVY UTERINE BLEEDING

CROSS-REFERENCE TO RELATED APPLICATIONS

This application is the national stage application of corresponding international application number PCT/IB2018/057778, filed Oct. 8, 2018, which claims priority to and the benefit of European application no. 17195397.9, filed Oct. 9, 2017, all of which are hereby incorporated by reference in their entirety.

TECHNICAL FIELD

The invention pertains to the technical field of absorbent hygiene products. In particular, the present invention relates to sanitary napkins employed to contain and retain menses and corporal fluids, specifically to sanitary napkins used for women with heavy uterine bleeding, which comprise an upper fluid-permeable layer, a lower fluid-impermeable layer, an absorbent core interposed between them and at least one pair of fold back wings; they may also have embossed channels to contribute to an efficient absorption and distribution of fluids.

BACKGROUND

Sanitary napkins are articles employed to absorb menses and corporal fluids. Nowadays there are many different sizes and configurations of said absorbent articles that may vary according to the needs of the user; for example, sanitary napkin for day use, sanitary napkin for night use, for light bleeding, for normal bleeding and for heavy bleeding. The sanitary napkins comprise an upper fluid-permeable layer, a lower fluid-impermeable layer, an absorbent core interposed between them and a fastening system used to attach the napkin to the undergarment of the user; in some cases said articles comprise fold back wings employed for protecting the lateral sides of the undergarment and for helping in maintaining the sanitary napkin in place during use. The attachment of the fold back wings to the crotch panel of the undergarment helps in the longitudinal alignment of the sanitary napkin on said clothes for fitting correctly to the body of the user. The extension of the sanitary napkin from the front edge to the rear edge will be determined directly by the position of the wings along the sanitary napkin. During use, if the sanitary napkin is too short toward the front and/or rear of the absorbent article, the risk of leaking increases and the user will feel unsafe. On the other hand, if the sanitary napkin is too long toward the front and/or rear half of the absorbent article the discretion is lost and in consequence the user will feel uncomfortable. Women with conditions such as Abnormal Uterine Bleeding (AUB) or menorrhagia present heavy bleeding, therefore they must use sanitary napkins with an adequate extension area in front and rear regions so that they feel safe, generally this kind of articles are not discreet. On the other hand, the sanitary napkins for heavy menstrual bleeding need also include an improved absorption system with an absorbent core with high absorbent capacity and with an efficient distribution of fluids, so that all this capacity can be used and leakage prevented. The sanitary napkin of the present invention is long enough to women feel secure and discreet enough to women feel comfortable, besides it has an absorbent core with high absorbent capacity, optionally with embossed channels designed specifically for an efficient distribution of fluids such that most of the absorption capacity of the core can be used. The position of the fold back wings may promote the correct placement not only of the longitudinal extension of the absorbent body but also the correct placement of the channels, so that the flow is distributed in both the front and rear portions of the sanitary napkin guided by the channels. Hence the wing construction not only addresses the problem of providing a secure and discreet article, but further also more generally aims at aiding in leakage prevention, like the channels do in significantly contributing to increase the absorbent capacity of the napkin.

There are some proposals in order to attend the needs of women with heavy menstrual bleeding such as the ones mentioned below:

For example, U.S. Pat. No. 7,708,725B2, refers to a sanitary napkin with a pair of front flaps, a pair of rear flaps and a pair of fold-back flaps between said front and back flaps, wherein a pair of anti-leakage barriers project transversely outward from the narrowest portion of the sanitary napkin body and don't project outward from the widest point of said sanitary napkin. However, this design increases the use of material in the anti-leakage barriers and does not focus on one of the most important aspects for the users, which is the fit and discretion of the absorbent article given by the position along said sanitary napkin of the fold back wings.

U.S. Pat. No. 9,125,772, describes a sanitary napkin comprising a front end region with a longitudinal extension between ¼ and ⅓ of the overall length of the absorbent article, a longitudinal subsection where the fold back wings are placed which must occupy less than ¼ of the overall longitudinal extension and a rear end region which occupies less than ⅕ of the overall extension of the sanitary napkin and in which a pair of rear fold back wings are placed, however said absorbent article has not enough extension in the rear region in order to make the user feel safe, as the rear region is too short to cover enough area of the rear portion of the body, especially when talking about sanitary napkin for heavy menstrual bleeding.

EP0731681, describes a sanitary napkin with fold back wings and arcuate channels in the central region of the absorbent body helping the absorbent article to assume a W-shape during use, wherein the fold back wings extend laterally outward from said central region; the article has a rear region being 1.5 to 2 times wider than the front region of it. The arcuate channels fail in increasing the absorption rate and fluid distribution along the article so that the sanitary napkin described in EP0731681 is not adequate for heavy menstrual bleeding.

On the other hand, plenty of research has been carried out in the use of channels for sanitary napkins; this is exemplified in the following publications U.S. Pat. No. 8,715,258B2, U.S. Pat. No. 5,795,345B1, U.S. Pat. No. 7,686,790B1, US2015265474A1, and WO201568718A1; however, these proposals still fail to improve the absorption rate and the distribution of the fluids within the absorbent core, especially for sanitary napkins used by women with AUB or menorrhagia.

Thus, there is a need of a sanitary napkin designed specifically for heavy menstrual bleeding, the napkins further designed to provide safeness to the user and that are not noticeable when using tight clothes, and improve the fluid handling and distribution of the body fluids in said absorbent core.

The present disclosure may address a number of currently unmet needs, for example to provide a sanitary napkin designed for be used by women with heavy uterine bleeding with front and rear portions long enough to be secure and discreet as a consequence of the position of the fold back wings along the sanitary napkin.

Another example is to provide a sanitary napkin with embossed channels specially designed to contribute in having high absorbent rate and an efficient distribution of fluids.

A further example is to provide a sanitary napkin designed for use by women with heavy uterine bleeding with front and rear portions long enough to be secure and discreet as a consequence of the position of the fold back wings along the sanitary napkin and with embossed channels specially designed to contribute in having high absorbent rate and an efficient distribution of fluids.

SUMMARY OF THE INVENTION

The present invention provides an absorbent sanitary napkin (1) comprising fold back wings (3) and an absorbent core (2) interposed between an upper fluid-permeable layer (4) and a lower fluid-impermeable layer (5), the sanitary napkin (1) having a longitudinal central axis (y-y) and a transverse central axis (o-o), a pair of transverse sides (10) and a pair of longitudinal sides (9) extending therebetween, a front edge (6) and a rear edge (7) positioned on opposite apexes of said transverse sides (10); the fold back wings (3) extending transversely beyond the longitudinal sides (9) of the sanitary napkin (1) and comprising a transverse axis (x-x) dividing said fold back wings (3) into two substantially equal halves in a longitudinal direction parallel to the longitudinal central axis (y-y), said transverse axis (x-x) of the fold back wings (3) being offset from the sanitary napkin transverse central axis (o-o) toward the front edge (6) of the sanitary napkin (1), characterized in that the fold back wings (3) are positioned along the sanitary napkin such that an overall length ratio corresponds to the following equation:

$$L^*(L1/L2)>29\text{ cm}$$

where L is the total length of the sanitary napkin taken along the longitudinal central axis (y-y), L1 is the distance from the transverse axis (x-x) of the fold back wings (3) to the front edge (6), and L2 is the distance from the transverse axis (x-x) of the fold back wings (3) to the rear edge (7).

In another aspect of the invention, the absorbent core (2) comprises a first elongated central closed channel (20) centered with respect to the longitudinal and transverse edges (25, 26) of the core oppositely disposed along the longitudinal central axis (y-y), wherein, the first elongated central closed channel (20) has an hourglass shape oriented such that a longest length thereof is substantially parallel to the longitudinal direction of the napkin (1), the absorbent core (2) further comprising at least two second longitudinal disconnected channels (21*a*,21*b*) centrally aligned on the longitudinal central axis (y-y) and separated along the longitudinal axis of the article by a separation distance of less than 20% of the length (e) of the elongated central closed channel (20), and wherein said disconnected longitudinal channels (21*a*,21*b*) are completely enclosed by said elongated central closed channel (20).

According to another aspect of the invention, the sanitary napkin (1) comprises fold back wings (3) and an absorbent core (2) interposed between an upper fluid-permeable layer (4) and a lower fluid-impermeable layer (5), the sanitary napkin (1) having a longitudinal central axis (y-y), a pair of transverse sides (10) and a pair of longitudinal sides (9) extending therebetween, a front edge (6) and a rear edge (7) positioned on opposite apexes of said transverse sides (10); the fold back wings (3) extending transversely beyond the longitudinal sides (9) of the sanitary napkin (1) and comprising a transverse axis (x-x) dividing said fold back wings (3) into two substantially equal halves in a longitudinal direction parallel to the longitudinal central axis (y-y), characterized in that the fold back wings (3) are positioned along the sanitary napkin such that an overall length ratio corresponds to the following equation:

$$L^*(L1/L2)>29\text{ cm}$$

where L is the total length of the sanitary napkin taken along the longitudinal central axis (y-y), L1 is the distance from the transverse axis (x-x) of the fold back wings (3) to the front edge (6), and L2 is the distance from the transverse axis (x-x) of the fold back wings to the rear edge (7); and in that the said transverse axis (x-x) of the fold back wings (3) is offset toward the front edge (6) of the sanitary napkin (1), from a sanitary napkin transversal axis (o-o) crossing the midpoint of said total length (L) and a first elongated central closed channel (20) centered with respect to the longitudinal and transverse edges (25, 26) of the core oppositely disposed along the longitudinal central axis (y-y), wherein, the first elongated central closed channel (20) has an hourglass shape oriented such that a longest length thereof is substantially parallel to the longitudinal direction of the napkin (1), the absorbent core (2) further comprising at least two second longitudinal disconnected channels (21*a*,21*b*) centrally aligned on the longitudinal central axis (y-y) and separated along the longitudinal axis of the article by a separation distance of less than 20% of the length (e) of the elongated central closed channel (20), and wherein said disconnected longitudinal channels (21*a*,21*b*) are completely enclosed by said elongated central closed channel (20).

DETAILED DESCRIPTION OF THE INVENTION

Figure 1:
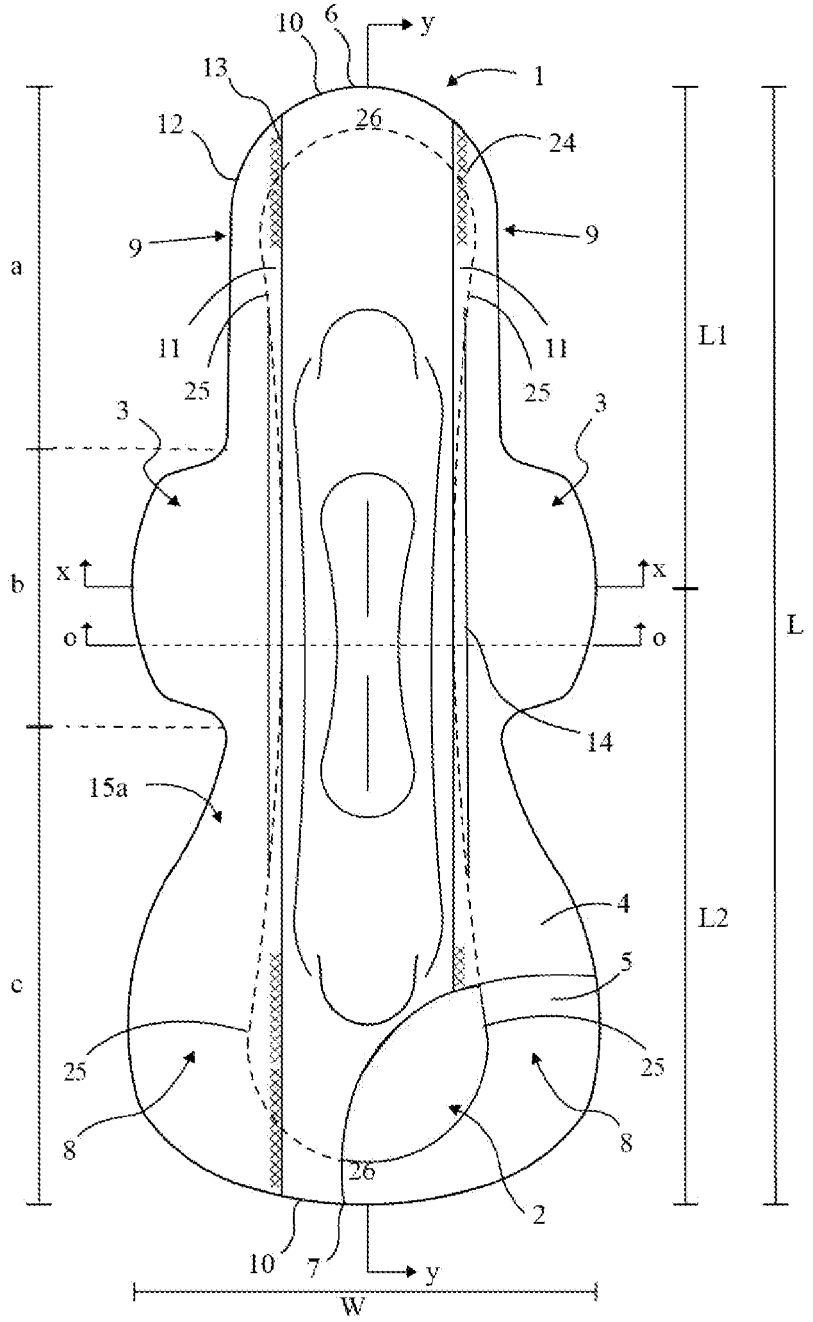
FIG. 1 illustrates a sanitary napkin according to an embodiment of the invention in extended form, showing the body facing surface.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein. Herein, "comprise" and "include" mean that other elements and/or other steps which do not affect the end result can be added. Each of these terms encompasses the terms "consisting of" and "consisting essentially of".

The expression "absorbent article" or "personal hygiene article" or "personal hygiene absorbent article" as used herein, refers to articles which are worn by females adjacent to the pudendal region which are intended to absorb and contain the various exudates which are discharged from the body (e.g., blood, menses, and urine) and is tended to include sanitary napkins, incontinence pads and pantyliners.

The expression "extended form" means an article in its laid-flat and fully stretched condition as illustrated in the figures herein.

The expression "body facing surface" refers to surfaces of absorbent articles and/or their component members which face the body of the wearer, while the term "garment facing surface" refers to the opposite surfaces of the absorbent articles and/or their component members that face away from the wearer when the absorbent articles are worn. Absorbent articles and components thereof, including the upper fluid-permeable layer, lower fluid-impermeable, absorbent core, and any individual layers of their components, have a body facing surface and garment facing surface.

The "lower fluid-impermeable layer", "baffle" or "back sheet" are used herein as synonyms, and is preferably liquid-impermeable, and preferably designed to permit the passage of air or vapor out of the absorbent article while blocking the passage of body fluid. A fluid-impermeable layer can be made from any material having these properties. The fluid-impermeable back sheet can also be constructed from a material that will block the passage of vapor as well as fluids, if desired. A suitable material from which the lower fluid-impermeable layer may be constructed is a micro-embossed, polymeric film, preferably a film comprising or consisting of a polyolefin, such as a polyethylene or a polypropylene. The film made with polyethylene, may be composed for at least 50 wt. % of a polyethylene, preferably for at least 75 wt. %, more preferably for at least 90 wt. %, even more preferably for at least 95 wt. %. Bicomponent films may also be used as a lower fluid-impermeable layer.

The "upper fluid-permeable layer" or "top sheet" as used herein as synonyms, is preferably liquid-permeable. The upper fluid-permeable layer is a non-woven substrate, a film or laminate comprising both materials (for example, one or more nonwoven layers laminated to one or more film layers). The materials may be left as a continuous layer or may be modified to three-dimensional, embossed, perforated webs or any other combination thereof. It may be bonded or associated to the lower fluid-impermeable layer using any known method which does not leave any hard or uncomfortable residues that would annoy the individual using the absorbent article. Those skilled in the art are familiar with methods of bonding the various materials and for bonding other materials comprised in the absorbent article as described herein, including but not limited to the use of pressure-sensitive adhesives, hot-melt adhesives, two-sided adhesive sheets, ultrasonic welding and heat sealing. Adhesives such as hot-melt adhesives may be applied uniformly or in the form of a continuous or non-continuous layer.

The "absorbent medium", "absorbent core" or "absorbent body" in the absorbent article is preferably disposed between an upper fluid-permeable layer and a lower fluid-impermeable layer and is capable of absorbing and retaining body exudates. The absorbent core may be manufactured in a wide variety of shapes (for example, rectangular, trapezoidal, T-shape, I-shape, hourglass shape, dog bone shape, etc.) and may comprise a wide variety of absorbent materials. Examples of absorbent materials include fluff pulp, preferably cellulosic fluff pulp, tissue layers, highly absorbent polymers (so called superabsorbent polymer particles or "SAP"), absorbent foam materials, absorbent nonwoven materials and the like, or any combination of two or more of these absorbent materials. The absorbent core may comprise one or more layers of absorbent material stacked on top of each other.

It is also possible that the absorbent article comprises an acquisition and distribution layer. "Acquisition and distribution layer", "ADL" or "surge management portion" refers to a layer, which preferably is a nonwoven wicking layer, preferably located below the upper fluid-permeable layer of an absorbent article, which further speeds up the transport and improves distribution of fluid throughout the absorbent core. The acquisition and distribution layer is typically less hydrophilic than the absorbent core, and has the ability to quickly collect and temporarily hold liquid surges, and to transport the liquid from its initial entrance point to other parts of the absorbent structure, particularly to other parts of the absorbent core. The acquisition and distribution layer may prevent or at least reduce the liquid from pooling and collecting on the portion of the absorbent article positioned against the individual's skin, thereby reducing the feeling of wetness by the individual. Preferably, the acquisition and distribution layer is positioned between the liquid permeable top sheet and the absorbent core.

The term "fold back wings" as used herein is preferably understood as a pair of flaps extending transversely beyond the longitudinal sides of the sanitary napkin. The fold back wings are folded downward along the lateral edges of the crotch panel of the user's undergarment and bonded to the external surface of this crotch panel when placing the sanitary napkin for being used. The fold back wings could be an extension of the upper fluid permeable layer and the lower fluid impermeable layer or could be separate elements, bonded to the longitudinal sides of the sanitary napkin.

The term "adhesive" as used herein is understood to include any suitable hot melt, water borne adhesive or solvent borne adhesive that can be applied to a surface of a film layer in a desired pattern or network of adhesive areas to form a film-nonwoven laminate. Accordingly, suitable adhesives include conventional hot melt adhesives, pressure-sensitive adhesives and reactive adhesives, such as for example a polyurethane adhesive.

The recitation of numerical ranges by endpoints includes all numbers and fractions subsumed within that range, as well as the recited endpoints.

The present invention is preferably directed to a sanitary napkin designed for be used by women with heavy uterine bleeding. Without wishing to be bound by theory, women with this condition need a sanitary napkin length enough for feeling secure and discreet enough for feeling comfortable. There are many products on the market of sanitary napkins but all such napkins that provide required security to women are not discreet. This is believed to be owing to the fold back wings being positioned in such a way that when placing the article on the undergarment, the rear portion of the napkin is too long, so that it is particularly noticeable when wearing tight clothing. On the other hand the sanitary napkins described herein may provide an efficient fluid distribution enhanced by the embossed channels specially designed for this purpose, so that all the absorbent capacity of the absorbent core is used.

The sanitary napkin of the present invention comprises an absorbent core interposed between an upper fluid-permeable layer and a lower fluid-impermeable layer and a pair of fold back wings. The sanitary napkin may further comprise anti-leakage barriers, transfer and/or acquisition and distribution layers, elastic zones and other elements known in the art.

The upper fluid-permeable layer and the lower fluid-impermeable layer which enclose said absorbent core are bonded or associated together using any known method in the art, included but not limited to adhesive bonding, ultrasonic welding and heat sealing. The bonded portion between the upper fluid-permeable layer and the lower fluid-impermeable layer defines the entire periphery of the sanitary napkin. The absorbent core has longitudinal and transverse edges placed inwardly from the longitudinal and transverse sides of the sanitary napkin, respectively, and the periphery of the absorbent article extends adjacent to said absorbent core. The transverse sides of the sanitary napkin define the front and rear edges of the same and the fold back wings extend from each of the longitudinal sides of the sanitary napkin.

Figure 2:
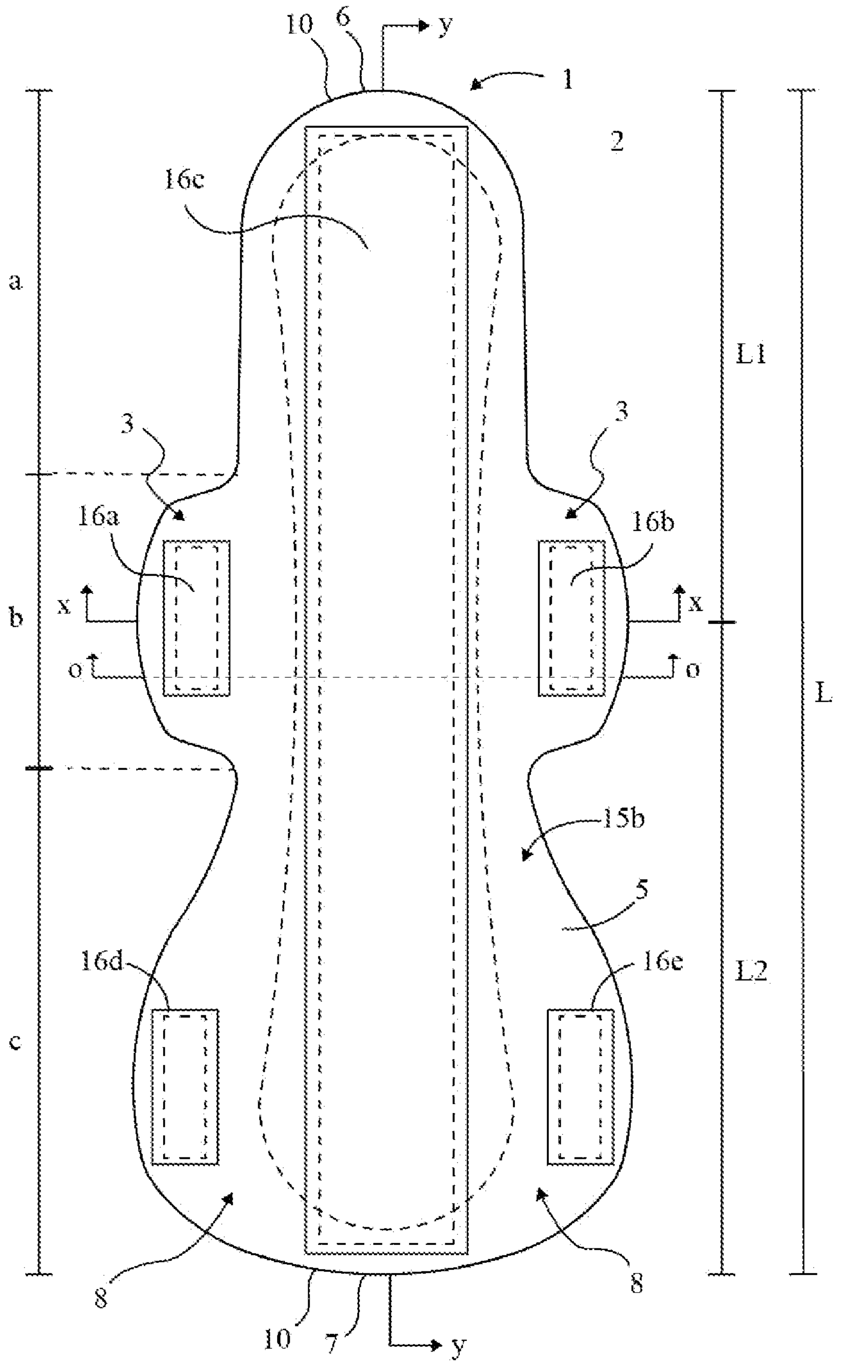
FIG. 2 illustrates the sanitary napkin of FIG. 1 in extended form, showing its garment facing surface.

FIG. 1 shows the sanitary napkin (1) according to an embodiment of the present invention in an extended form, showing its body facing surface (15*a*). As can be seen, the sanitary napkin (1) may comprise a pair of fold back wings (3) and an absorbent core (2) interposed between an upper fluid-permeable layer (4) and lower fluid-impermeable layer (5). The absorbent article may comprise two opposite longitudinal sides (9) and two opposite transverse sides (10); the pair of fold back wings (3) which extend from the longitudinal sides (9) of the sanitary napkin (1) may be positioned in the central portion (b) of it, for the purposes of the invention, this central portion (b) is preferably not aligned with a central transverse axis. The sanitary napkin may comprise fastening means (16) as can be seen in FIG. 2, for attaching it to the underwear of the undergarment of the user when placing the napkin on it.

The sanitary napkin (1) has a longitudinal central axis (y-y) centered on the total width W of the absorbent core (2) and by a transverse central axis (o-o) centered on the total length L of the absorbent core (2).

The fold back wings (3) can be either integrally formed with the sanitary napkin as a prolongation of the upper fluid-permeable layer (4) and the lower fluid-impermeable layer (5), or being separate elements bonded to the longitudinal sides (9) of the napkin.

For explanation purposes, the sanitary napkin (1) may be divided into a front portion (a), a rear portion (c) and a central portion (b) between them. The central portion (b) is defined by the length of the fold back wings (3) taken in the point in which they extend from the longitudinal sides (9) of the sanitary napkin (1) in a direction parallel to the longitudinal axis (y-y). The front portion (a) is the portion of the sanitary napkin placed frontward and immediately adjacent to the central portion (b), the rear portion (c) is the portion of the sanitary napkin placed rearward and immediately adjacent to the central portion (b).

The sanitary napkin (1) of the invention is preferably designed to be used by women with heavy uterine bleeding, as said, women with this condition need a sanitary napkin long enough for feeling secure and discreet enough for feeling comfortable. The position of the fold back wings (3) along the article in long napkins designed for night use and/or for heavy uterine bleeding is beneficial for the napkin being comfortable and discreet.

The total length L of the sanitary napkin of the present invention is given by the length taken along the central longitudinal axis (y-y) from the front and rear edges (6, 7) of said sanitary napkin. Said total length L may be between 25 and 40 cm, preferably between 27 and 39 cm and more preferably between 30 and 38 cm, in order to have an adequate extension for the absorption of menses of a person with heavy uterine bleeding.

For the purposes of this invention, the fold back wings (3) are divided by a transverse axis (x-x) in two substantially equal halves in the longitudinal direction parallel to the longitudinal central axis (y-y), as seen in FIG. 1. L1 is the distance from the transverse axis (x-x) of the fold back wings (3) to the front edge (6) of the napkin and L2 is the distance from the transverse axis (x-x) of the fold back wings (3) to the rear edge (7) of the napkin.

The fold back wings (3) of the sanitary napkin (1) of the invention are positioned along the longitudinal sides (9) of the article, so that the overall length ratio L*(L1/L2) is greater than 29 cm, preferably greater than 30 cm, more preferably from 33 to 40 cm and even more preferably from 34 to 36 cm. It has been surprisingly found that in this way the position of the fold back wings (3) along the napkin ensure that it will not be noticed when the napkin is used with tight pants or jeans owing to this specific positioning of the fold back wings (3), whilst at the same time makes the rear portion (c) of the napkin long enough to give enough protection to the user, but no too long to be noticed trough the clothes. Benefits of sanitary napkins according to embodiments of the invention compared to products on the market today can be seen in Example 1 hereinbelow.

In an embodiment of the present invention, the rear portion (c) of the sanitary napkin (1) comprises rear flaps (8) extending beyond the longitudinal edges (25) of the absorbent core (2). These rear flaps (8) may have the same width as the fold back wings (3) or could be wider than the fold back wings (3). Moreover, the rear flaps (8) may have fastening means (16*e*,16*d*) on the garment facing surface (15*b*) of the napkin to be attached to the inner surface of the underwear of the user when placing the napkin on it.

The length of the rear flaps (8) is taken in the point in which they extend from the longitudinal sides (9) of the sanitary napkin (1) in a direction parallel to the longitudinal axis (y-y).

In an embodiment the length of the rear flaps (8) is at least 28% of the total length (L) of the sanitary napkin, preferably between 30% and 45% of the total length of the sanitary napkin, more preferably between 35% and 43% of the total length of the sanitary napkin.

In another embodiment, or in addition to the latter embodiment, the length of the fold back wings (3) is at most 90%, preferably at most 85% or at most 80%, more preferably at most 75%, of the length of the rear flaps (8).

This may allow to give enough leakage protection to the user whilst not being noticeable trough the clothes.

In a preferred embodiment the rear flaps (8) have a length substantially equal to the length of the rear portion (c).

Figure 3:
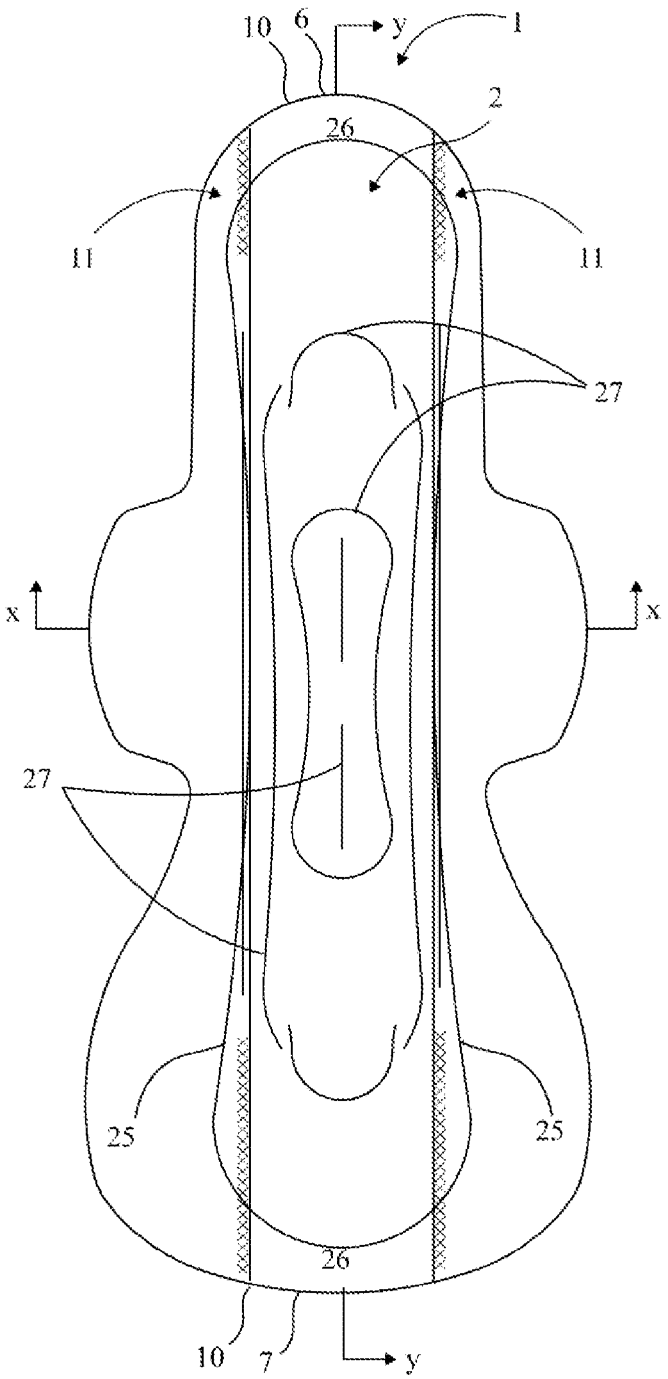
FIG. 3 shows the sanitary napkin according to an embodiment of the invention in extended form, showing the embossed channels.

As is shown in FIG. 3, the sanitary napkin (1) of the invention preferably comprises channels (27) (that are preferably embossed) on the upper fluid permeable layer (4) and on the absorbent core (2). These channels are particularly designed to contribute in the distribution of fluids and, as a result, the absorbent capacity of the article is increased because the area of the absorbent core that is used is increased.

The sanitary napkin (1) of the invention typically absorbs at least 7 g of synthetic menstrual fluid per gram of absorbent core measured according to the test method described below. Other sanitary napkins designed for heavy uterine bleeding actually on the market today like Always Maxi Extra Heavy from Procter & Gamble, Sofy Ultra Fit from Uni Charm Corporation, Laurier form Kao Corp. and Kotex Maxi form Kimberly Clark, as compared to a sanitary napkin according to an embodiment of the present invention can be seen in Example 2 hereinbelow.

Figure 5:
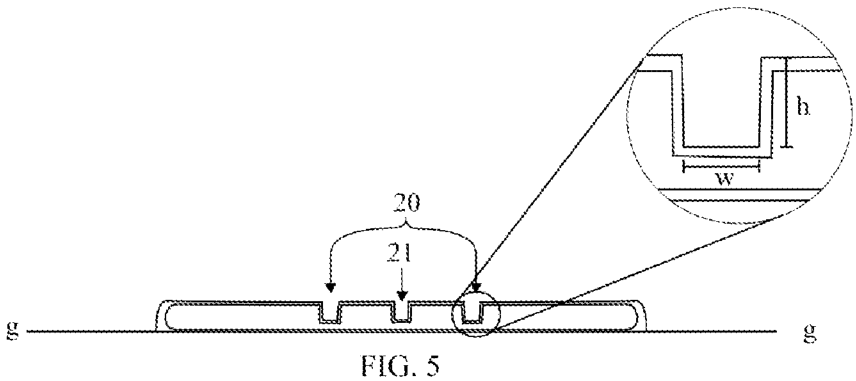
FIG. 5 is a sectional view of the sanitary napkin of FIG. 4*a* along the line g.

Preferably, as can be seen in FIG. 5, the channels (27) have a depth (h) between 4 and 7 mm and a width (w) between 2 and 4 mm, these dimensions are desirable to achieve the showed results in Example 2. Typically said channels (27) are embossed on the upper fluid permeable layer and on the absorbent core.

Figure 4A:
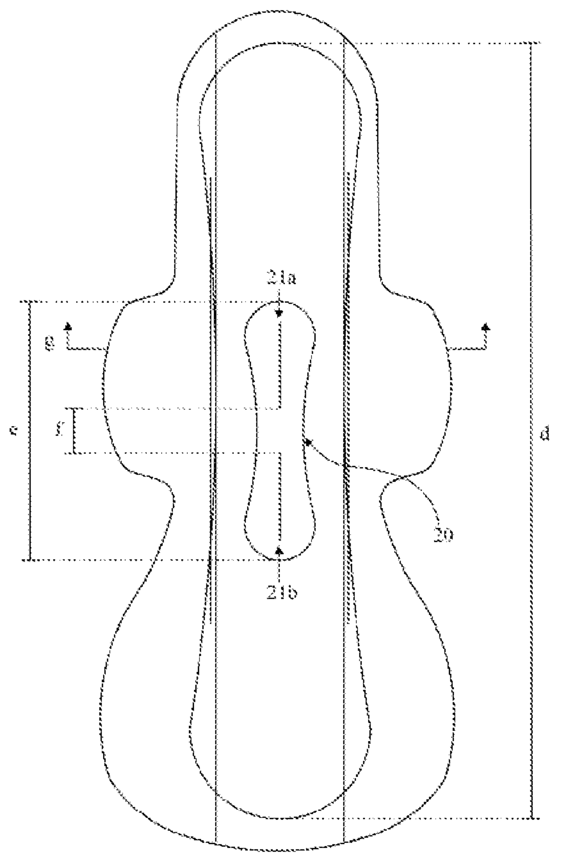
FIGS. 4*a* to 4*c* show three different configurations of the embossed channels of the sanitary napkin of an embodiment of the present invention.
Figure 4B:
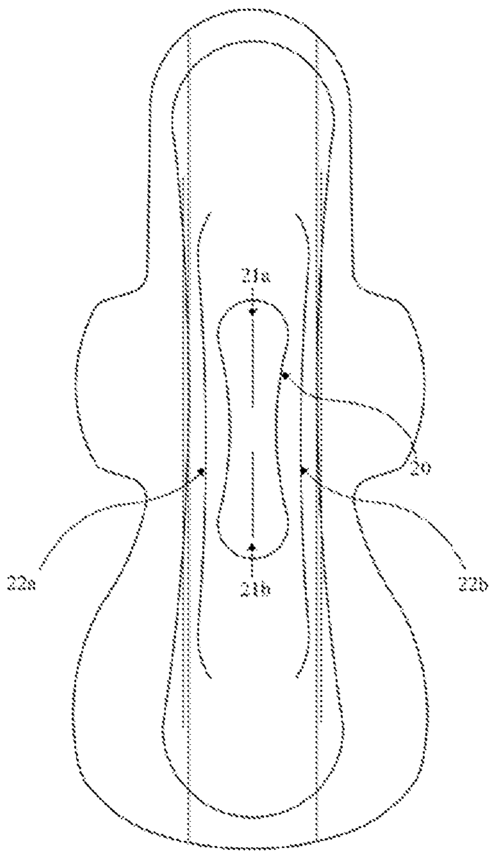
Figure 4C:
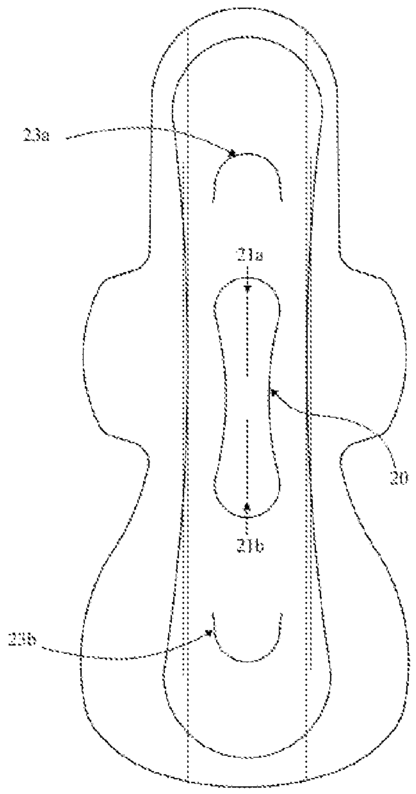

FIGS. 4*a* to 4*c* show three exemplary configurations of the embossed channels of the sanitary napkin of an embodiment of the present invention.

Preferably, the first channel, as can be seen in FIG. 4*a*, is an elongated central closed channel (20) with an hourglass shape oriented such that a longest length thereof is substantially parallel to the longitudinal direction of the napkin (1); this elongated central closed channel (20) preferably has a maximum length (e) taken along the longitudinal central axis (y-y), less than 50% of the total length of the absorbent core (d). The second channels showed in FIG. 4*a* preferably comprise at least two (typically only two) disconnected longitudinal channels (21*a*,21*b*) centrally aligned on the longitudinal central axis (y-y) and separated along the longitudinal axis of the article by a separation distance (f) of preferably less than 20%, more preferably from 5% to 15%, of the total length (e) of the elongated central closed channel (20). Without being bound by theory it is believed that if length e is too great fluid distribution speed is greatly reduced, on the other hand if too small fluid immediately flows towards the ends of the channels without promoting even absorption in the central portion of the core along the transverse axis direction.

The second channels (21*a*,21*b*) are preferably completely enclosed by said elongated central closed channel (20). The described configuration of the first and second channels of an embodiment of the present invention, contributes significantly to increase the absorbent capacity of the napkin given that when the fluid is deposited on the napkin, the two disconnected longitudinal channels help in the rapid absorption and distribution of this fluid toward the front and rear portions of the napkin; when the fluid reaches the central closed channel (20), it delay the pass of the fluid to the area of the absorbent core outside this central closed channel (20) until the area inside the central closed channel (20) is saturated, then the fluid begins to reach other portions of the napkin.

Preferably, the sanitary napkin has additional channels typically embossed on the upper fluid permeable layer (4) and on the absorbent core (2), that extend beyond and outside of the elongated central embossed channel (20). One embodiment of these additional channels are showed in FIG. 4*b*, which includes the first and second channels (20,21*a* and 21*b*) and the additional channels. These additional channels comprise at least two longitudinal channels (22*a*,22*b*) preferably embossed adjacent oppositely disposed longitudinal edges (25) of the absorbent core (2), and positioned between the elongated central closed channel (20) and each of said longitudinal edges (25) of the absorbent core. These longitudinal channels (22*a*, 22*b*) are preferably longer than the elongated central closed channel (20) and could be straight lines parallel to the longitudinal central axis (y-y), concave curved or convex curved as showed in FIG. 4*b*. These additional longitudinal channels (22*a*,22*b*) delay the pass of the fluid to the longitudinal edges (25) of the absorbent core and help in distributing the fluid toward front (a) and rear (b) portions of the sanitary napkin.

FIG. 4*c* shows another embodiment of the additional embossed channels of the sanitary napkin (1) of the present invention. These additional channels comprise two end semicircular channels (23*a*,23*b*) typically embossed on the upper fluid permeable layer (4) and on the absorbent core (2) proximal to the front (a) and rear (c) portions of the sanitary napkin (1) and oriented such that a concave portion thereof faces toward the transverse axis (x-x). These end semicircular channels (23*a*,23*b*), help in delaying the pass of the fluid to the front (a) and rear (c) portions of the sanitary napkin until all the area between them is saturated with fluid helping thus to an efficient use of the absorbent core (2) and avoiding leakages from the front and rear ends of it.

In another embodiment of the sanitary napkin (1) of the invention, it comprises the first elongated central closed embossed channel (20), the two disconnected longitudinal channels (21*a*,21*b*), the longitudinal channels (22*a*,22*b*) and the end semicircular channels (23*a*,23*b*).

According to another embodiment of the invention, the sanitary napkin (1), comprises the fold back wings positioned along it such that an overall length ratio corresponding to the equation L*(L1/L2) is greater to 29 cm, preferably is greater than 30 cm, more preferably is greater than 32 cm, even more preferably is between 33 and 40 cm and even more preferably is between 34 and 36 cm and one or more of the embossed channels described above.

In one more embodiment of the invention, the sanitary napkin (1) comprising fold back wings (3) positioned as described in any of the embodiments of the invention and/or embossed channels as described in any of the embodiments of the invention, comprises longitudinal anti-leakage barriers (11) placed adjacent each longitudinal side (9) of the napkin, preferably the barriers (11) each have proximal edge (12) joinable to the upper fluid permeable layer (4) and a distal edge (13) comprising at least one elastic member (14). The anti-leakage barriers are preferably formed from a layer of an hydrophobic nonwoven sheet which could be extended to the longitudinal sides (9) of the sanitary napkin (1) forming the upper surface of the fold back wings (3).

Test Methods

Absorbent Capacity

Materials:

Synthetic menstrual fluid (500 ml)

500 ml Plastic Funnel

Sanitary Napkins

Procedure:

1. Prepare the synthetic menstrual fluid.
2. Weight a sanitary napkin and record this weight as W1.
3. Fill the plastic funnel with 500 ml of synthetic menstrual fluid and calibrate the flow rate to 0.66 ml/sec.
4. Pour the synthetic menstrual fluid at the calibrated flow rate on the middle point of the sanitary napkin (longitudinally and transversely) at a distance of 2.54 cm from the upper fluid permeable layer.
5. Stop the pouring when the fluid extends beyond the absorbent core at any point of the core edges.
6. Weight the sanitary napkin and record the weight as W2.

7. Separate all the elements of five sanitary napkins as the used for points 2 to 6 and weight the absorbent core of each one, calculate the average weight of the five absorbent cores and record it as W3
8. Calculate the absorbent capacity, expressed in g of synthetic menstrual fluid/g of absorbent core, as:

$$\text{Absorbent Capacity}=(W2-W1)/W3$$

Preparation of the Synthetic Menstrual Fluid:
Materials:

833 ml Propylene glycol 167 ml saline water (15 g NaCl in 167 ml of distilled water)

Artificial colorant

Procedure:

1. Mix vigorously the propylene glycol and the saline water.
2. Add to the mixture artificial color until the desired color is achieved.
3. Let stand the mixture for two hours at 20° C. before use it.

EXAMPLES

Example 1

Example A

A sanitary napkin according to an embodiment of the present invention is prepared having the dimensions indicated in Table 1.

TABLE 1

| Dimension (referencing the figures) | Size (cm) |
|---|---|
| L | 40 |
| L1 | 18.5 |
| L2 | 21.5 |
| a | 12.45 |
| b | 11.14 |
| c | 16.41 |

The sanitary napkin of Example A is then compared with other sanitary napkins on the market today. Table 2 shows a comparative analysis of the overall length ratio L*(L1/L2) of different sanitary napkins designed for night and/or for heavy uterine bleeding available on the market today:

TABLE 2

| Sanitary napkin | Total length L (cm) | L1 (cm) | L2 (cm) | L*(L1/L2) |
|---|---|---|---|---|
| Example A | 40 | 18.5 | 21.5 | 34.41 |
| Kotex unika night[1] | 30 | 13.5 | 16.5 | 24.54 |
| Kotex maxi day&night[1] | 30.3 | 13.9 | 16.4 | 25.68 |
| Kotex night thin[1] | 30 | 13 | 17 | 22.94 |
| Kotex night[1] | 31.4 | 14.5 | 16.9 | 26.94 |
| Always ultra thin night[2] | 31.5 | 12.8 | 18.8 | 21.42 |
| Always ultrathin extra heavy[2] | 37.5 | 13.4 | 22.3 | 22.53 |
| Always extra large[2] | 38.5 | 14.25 | 24.25 | 22.62 |
| Always maxi extra heavy[2] | 38 | 14 | 24 | 22.16 |

1 Produced and available by the Kimberly-Clark Corporation

2 Produced and available by the Procter & Gamble Company

As can be seen from table 2, the sanitary napkin according to an embodiment of the invention (Example A) has the highest overall length ratio L*(L1/L2).

Example 2

Example B

A sanitary napkin according to an embodiment of the present invention is prepared having the channel configuration indicated in Table 3

TABLE 3

| Dimension (referencing the figures) | Size (cm) |
|---|---|
| Channels 21a, 21b | 4.11 |
| Channels 22a, 22b | 22.15 |
| d | 37 |
| e | 12.5 |
| f | 2.14 |
| h | 0.16 |
| w | 0.08 |

The sanitary napkins are then tested for absorbent capacity according to the method described herein, and the results are shown in Table 4.

TABLE 4

| BRAND | TOTAL LENGTH (cm) | TOTAL CORE WEIGH (g) | ABSORBENT CAPACITY OF THE CORE (g of synthetic menstrual fluid/g absorbent core) |
|---|---|---|---|
| ALWAYS MAXI EXTRA HEAVY | 38 | 16.7 | 2.5 |
| SOFY ULTRA FIT | 40 | 13 | 5.5 |
| LAURIER | 39 | 12 | 4.5 |
| KOTEX NIGHT | 31.4 | 10 | 2.5 |
| EXAMPLE B | 40 | 14 | >7 |

It is important to say that the absorbent cores of all the tested sanitary napkins in Table 4, are similar in that they do not contain superabsorbent particles, some of them have core wrap layer and/or transfer layer(s). Example B on the other hand does not comprise wrap or transfer layer(s), hence the findings are even more remarkable. The results in Table 4 show that the embossed channels (27) in Example B are effective in distributing the fluids along the absorbent core (2) so that a larger area of the absorbent core is used and the absorbent capacity, expressed as g of synthetic menstrual fluid/g absorbent core, is increased.

Use test are then conducted with women suffering of abnormal uterine bleeding, they are provided with one embodiment of sanitary napkin of the invention with fold back wings (3) positioned as Example A and embossed channels (27) as those of Example B and they are requested to give their opinion about comfortability, security and discretion. The results show that 100% of the users rate the napkin as comfortable, secure and discreet.

Although the invention submitted is described in detail in function of the preferred forms of implementation, it is not restricted to other forms of implementation and additional modifications that are within the spirit and scopes thereof, being evident that these are included within the same. In the same way claims are appended with the scopes that could present the invention.

The invention claimed is:

1. An absorbent sanitary napkin (1) comprising fold back wings (3) and an absorbent core (2) interposed between an upper fluid-permeable layer (4) and a lower fluid-impermeable layer (5), the sanitary napkin (1) having a longitudinal central axis (y-y) and a transverse central axis (o-o), a pair of transverse sides (10) and a pair of longitudinal sides (9) extending therebetween, a front edge (6) and a rear edge (7) positioned on opposite apexes of said transverse sides (10); the fold back wings (3) extending transversely beyond the longitudinal sides (9) of the sanitary napkin (1) and comprising a transverse axis (x-x) dividing said fold back wings (3) into two substantially equal halves in a longitudinal direction parallel to the longitudinal central axis (y-y), said transverse axis (x-x) of the fold back wings (3) being offset from the sanitary napkin transverse central axis (o-o) toward the front edge (6) of the sanitary napkin (1), characterized in that the fold back wings (3) are positioned along the sanitary napkin such that an overall length ratio corresponds to the following equation:

$$L^*(L1/L2)>29\text{ cm}$$

where L is the total length of the sanitary napkin taken along the longitudinal central axis (y-y), said total length L is between 25 and 40 cm, L1 is the distance from the transverse axis (x-x) of the fold back wings (3) to the front edge (6), and L2 is the distance from the transverse axis (x-x) of the fold back wings (3) to the rear edge (7).

2. The absorbent sanitary napkin (1) according to claim 1, wherein the overall length ratio is greater than 30 cm.

3. The absorbent sanitary napkin according to claim 1, wherein the fold back wings (3) are integrally formed with the sanitary napkin as a prolongation of the upper fluid-permeable layer (4) and the lower fluid-permeable layer (5) or are separate elements bonded to the longitudinal sides (9) of the napkin.

4. The absorbent sanitary napkin according to claim 1, wherein the sanitary napkin has a front portion (a), a rear portion (c) and a central portion (b) extending therebetween, and wherein the rear portion (c) has rear flaps (8) extending beyond longitudinal edges of the core (25).

5. The absorbent sanitary napkin according to claim 4, wherein the rear flaps (8) are wider in a transverse axis of the napkin than fold back wings (3).

6. The absorbent sanitary napkin according to claim 4, wherein the rear flaps (8) have a length in a direction parallel to the longitudinal axis (y-y), which is at least 28% of the total length (L) of the sanitary napkin.

7. The absorbent sanitary napkin according to claim 1, wherein the absorbent core (2) comprises an elongated central closed channel (20) centered with respect to the longitudinal and transverse edges (25, 26) of the core oppositely disposed along the longitudinal central axis (y-y), the absorbent core (2) further comprising at least two longitudinal channels disconnected between them (21 *a*, 21 *b*), wherein the elongated central closed channel (20) has an hourglass shape oriented such that a longest length thereof is substantially parallel to the longitudinal direction of the napkin (1), and wherein said disconnected longitudinal channels (21 *a*, 21 *b*) are centrally aligned on the longitudinal central axis (y-y), separated along the longitudinal axis of the article by a separation distance (f) of less than 20% of the length (e) of the elongated central closed channel (20), and completely enclosed by said elongated central closed channel (20), wherein the elongated central closed channel (20) and disconnected longitudinal channels (21 *a*, 21 *b*) are embossed on the upper fluid-permeable layer and on the absorbent core (2).

8. The absorbent sanitary napkin according to claim 7, wherein the elongated central closed channel (20) has a maximum length (e) taken along the longitudinal central axis (y-y) of less than 50% of the length of the absorbent core (d) taken along the longitudinal central axis (y-y).

9. The absorbent sanitary napkin according to claim 7, wherein the absorbent core (2) has one or more additional channels, that extend beyond and outside of the elongated central closed channel (20).

10. The absorbent sanitary napkin according to claim 9, wherein the additional channels comprise at least two longitudinal channels (22*a*, 22*b*), adjacent to oppositely disposed longitudinal edges (25) of the absorbent core (2), and positioned between the elongated central closed channel (20) and each of said longitudinal edges (25) of the absorbent core.

11. The absorbent sanitary napkin according (1) to claim 9, wherein the additional channels comprise at least two end semicircular channels (23*a*, 23*b*), proximal to the front (a) and rear (c) portions of the napkin (1), and oriented such that a concave portion thereof faces towards the transverse axis (x-x).

12. The absorbent sanitary napkin (1) according to claim 9 wherein the additional channels consist of a pair of longitudinal channels (22*a*, 22*b*) adjacent to oppositely disposed longitudinal edges (25) of the absorbent core (2), and positioned between the elongated central closed channel (20) and each of said longitudinal edges (25) of the absorbent core and a pair of end semicircular channels (23*a*, 23*b*) proximal to the front (a) and rear (c) portions of the napkin (1), and oriented such that a concave portion thereof faces towards the transverse axis (x-x).

13. The absorbent sanitary napkin (1) according to claim 1, wherein said napkin (1) comprises longitudinal anti-leakage barriers (11) placed adjacent each longitudinal side (9) of the napkin.

14. The absorbent sanitary napkin (1) according to claim 1, wherein the overall length ratio is greater than 32 cm.

15. The absorbent sanitary napkin (1) according to claim 1, wherein the overall length ratio is from greater than 33 to and less than 40 cm.

16. The absorbent sanitary napkin (1) according to claim 1, wherein the overall length ratio is from 34 to 36 cm.

17. The absorbent sanitary napkin (1) according to claim 13, wherein the barriers each have a proximal edge (12) joinable to the upper fluid-permeable layer (4) and a distal edge (13) comprising at least one elastic member (14).

* * * * *